United States Patent
Schurzig (10) Patent No.: US 11,006,229 B2
(45) Date of Patent: May 11, 2021

(54) MIDDLE EAR IMPLANT COUPLER FOR MECHANICAL COCHLEA STIMULATION VIA THE ROUND WINDOW

(71) Applicant: MED-EL Elektromedizinische Geraete GmbH, Innsbruck (AT)

(72) Inventor: Daniel Schurzig, Hannover (DE)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 16/482,319

(22) PCT Filed: Feb. 23, 2018

(86) PCT No.: PCT/US2018/019375
§ 371 (c)(1),
(2) Date: Jul. 31, 2019

(87) PCT Pub. No.: WO2018/156867
PCT Pub. Date: Aug. 30, 2018

(65) Prior Publication Data
US 2019/0356995 A1 Nov. 21, 2019

Related U.S. Application Data (60) Provisional application No. 62/463,763, filed on Feb. 27, 2017.

(51) Int. Cl.
*H04R 25/00* (2006.01)
*A61N 1/36* (2006.01)
*H04R 25/02* (2006.01)

(52) U.S. Cl.
CPC ....... *H04R 25/606* (2013.01); *A61N 1/36038* (2017.08); *H04R 25/02* (2013.01)

(58) Field of Classification Search
CPC .......................... H04R 25/606; H04R 2225/67
See application file for complete search history.

(56) References Cited

U.S. PATENT DOCUMENTS

| 4,645,504 A | * | 2/1987 | Byers | ........................ | A61F 2/00 |
| | | | | | 623/10 |
| 5,318,502 A | | 6/1994 | Gilman | | |
| (Continued) | | | | | |

FOREIGN PATENT DOCUMENTS

| WO | WO 2012/118725 A1 | 9/2012 |
| WO | WO 2014/204880 A1 | 12/2014 |

OTHER PUBLICATIONS

International Searching Authority/US, International Search Report and the Written Opinion of the International Searching Authority, Application No. PCT/US2018/019375, dated Apr. 26, 2018, 16 pages.

(Continued)

*Primary Examiner* — Ryan Robinson
(74) *Attorney, Agent, or Firm* — Sunstein LLP (57) ABSTRACT

A round window coupling device is described for a hybrid electric-mechanical stimulation hearing implant system. A rigid outer shell securely fits into a round window niche in a cochlear outer surface of a recipient patient. An electrode groove in the outer surface of the outer shell snuggly fits around a portion of a cochlear implant electrode array passing through the round window niche. A coupling filling is enclosed within the outer shell to couple mechanical vibrations from the proximal end to the distal end with minimal attenuation. A transducer receiver at the proximal end connects to and receives vibrations from a drive surface of a mechanical transducer. And a drive face at the distal end interfaces to perilymph fluid within the cochlea of the recipient patient to deliver vibrations from the coupling (Continued)

filling to the perilymph fluid with minimal attenuation for perception as sound.

9 Claims, 6 Drawing Sheets

(56) References Cited

U.S. PATENT DOCUMENTS

| | | | | |
|---|---|---|---|---|
| 5,782,744 | A * | 7/1998 | Money | H04R 25/606 600/25 |
| 6,259,951 | B1 * | 7/2001 | Kuzma | A61N 1/36038 607/57 |
| 6,628,991 | B2 * | 9/2003 | Kuzma | A61N 1/0541 607/137 |
| 6,889,094 | B1 * | 5/2005 | Kuzma | A61N 1/0541 607/137 |
| 7,283,874 | B2 * | 10/2007 | Penner | A61N 1/3718 607/33 |
| 8,285,384 | B2 * | 10/2012 | Ball | A61N 1/0541 607/57 |
| 8,396,570 | B2 * | 3/2013 | Dadd | A61N 5/0622 607/137 |
| 8,771,167 | B2 * | 7/2014 | Grasso | H04R 25/606 600/25 |
| 10,057,696 | B2 * | 8/2018 | Cho | H04R 25/606 |
| 10,661,075 | B2 * | 5/2020 | Schachtele | A61N 1/0541 |
| 2009/0240099 | A1 * | 9/2009 | Conn | A61N 1/0541 600/25 |
| 2009/0306458 | A1 | 12/2009 | Parker et al. | |
| 2010/0324355 | A1 * | 12/2010 | Spitaels | A61N 1/36038 600/25 |
| 2011/0295053 | A1 * | 12/2011 | Ball | H04R 25/606 600/25 |
| 2012/0071957 | A1 | 3/2012 | Carter | |
| 2017/0180889 | A1 * | 6/2017 | Walraevens | H04R 25/606 |
| 2017/0347209 | A1 * | 11/2017 | Heasman | H04R 25/606 |

OTHER PUBLICATIONS

European Patent Office, Extended European Search Report, Application No. 18758163.2, dated Jan. 21, 2020, 8 pages.
Geoffrey J. Service et al., *Alternative placement of the floating mass transducer in implanting the MED-EL Vibrant Soundbridge*, Operative Techniques in Otolaryngology—Head and Neck Surgery, W.B. Saunders, Amsterdam, NL, vol. 21, No. 3, Sep. 1, 2010, pp. 194-196, XP027541886, ISSN: 1043-1810.

* cited by examiner

MIDDLE EAR IMPLANT COUPLER FOR MECHANICAL COCHLEA STIMULATION VIA THE ROUND WINDOW

This application claims priority from U.S. Provisional Patent Application, filed Feb. 27, 2017, which is incorporated herein by reference in its entirety.

TECHNICAL FIELD

The present invention relates to hearing implants and specifically an arrangement for electromechanical stimulation using a middle ear transducer and cochlear implant.

BACKGROUND ART

Figure 1:
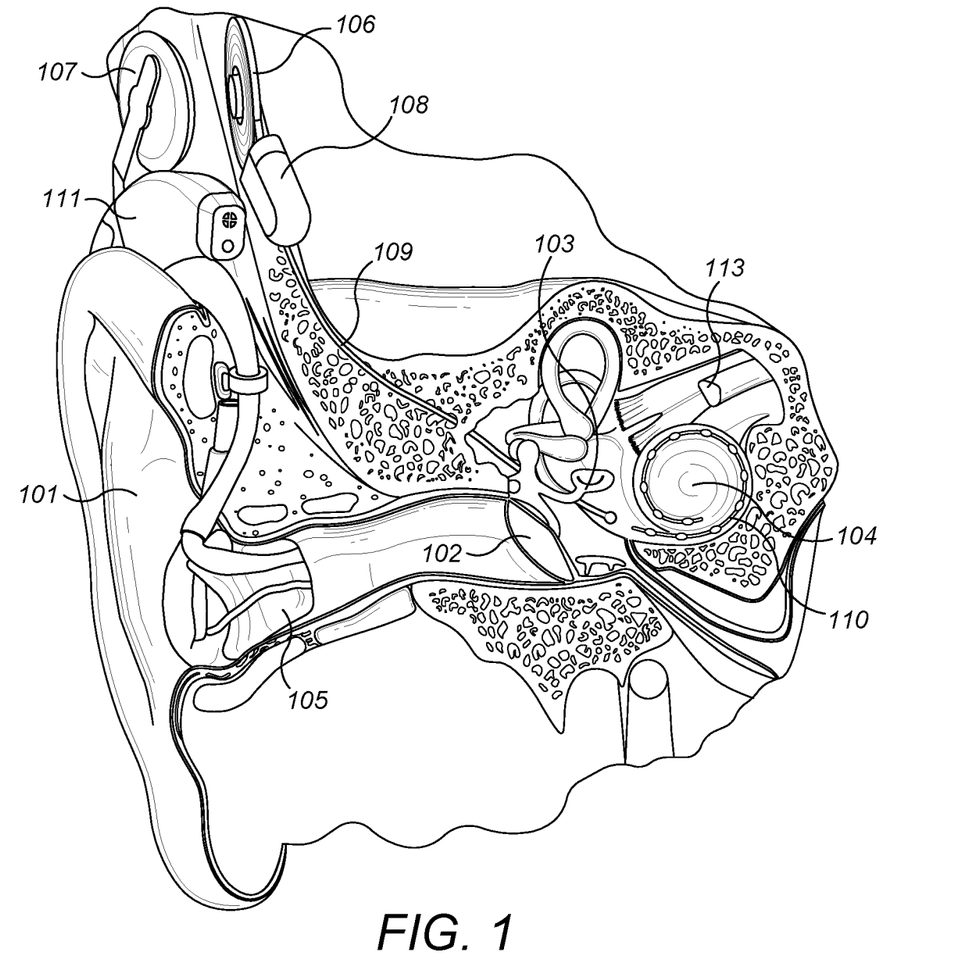
FIG. 1 shows the anatomy of a human ear and various structures in a middle ear hearing implant system.

A normal ear transmits sounds as shown in FIG. 1 through the outer ear 101 to the tympanic membrane 102 which moves the bones of the middle ear 103 (malleus, incus, and stapes) that vibrate the oval window and round window membrane openings of the cochlea 104. The cochlea 104 is a long narrow duct wound spirally about its axis for approximately two and a half turns in a human cochlea. It includes an upper channel known as the scala vestibuli and a lower channel known as the scala tympani, which are connected by the cochlear duct. The axial center of the cochlea 104 is called the modiolus where the spiral ganglion cells of the acoustic nerve 113 reside. In response to received sounds transmitted by the middle ear 103, the fluid-filled cochlea 104 functions as a transducer to generate electric pulses which are sensed by the acoustic nerve 113 and sent to the brain.

Figure 2:
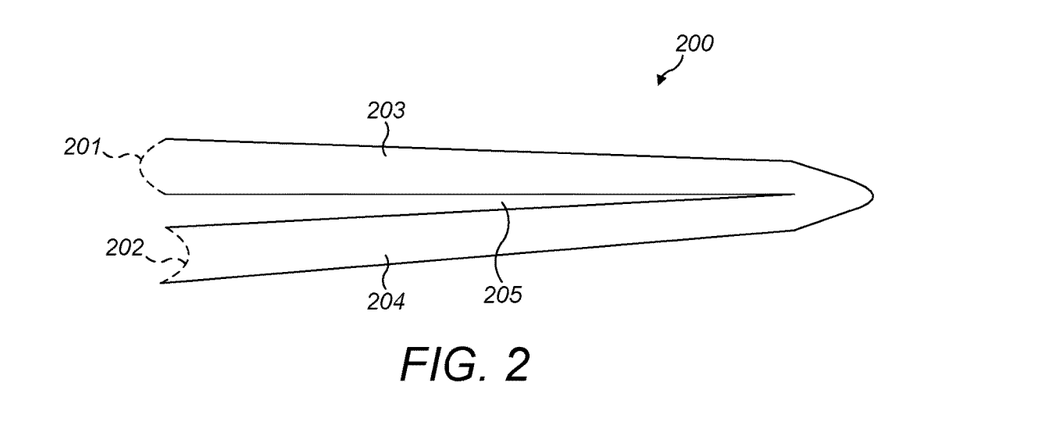
FIG. 2 shows a functional representation of a normal cochlea.

FIG. 2 shows a functional representation of a normal cochlea 200. The oval window membrane 201 comprises of a stiff center (stapes footplate) and a flexible surrounding across the opening to the fluid filled scala vestibuli 203. Vibration from the footplate of the stapes drives the oval window membrane 203 creating pressure wave vibration in the fluid of scala vestibuli 203. This in turn creates sympathetic pressure wave vibration in the fluid filled scala tympani 204 on the other side of the basilar membrane 205. The pressure wave vibration of the fluid in the scala tympani 204 in turn drives the membrane of the round window membrane 202 with a frequency phase shift of for example 180 degrees at low frequencies from the vibration of the oval window membrane 201.

Hearing is impaired when there are problems in the ability to transduce external sounds into meaningful action potentials along the neural substrate of the cochlea. To improve impaired hearing, hearing prostheses have been developed. For example, when the impairment is related to conductive hearing loss, a conventional hearing aid may be used to provide acoustic-mechanical stimulation to the auditory system in the form of amplified sound to the tympanic membrane. Or when the hearing impairment is associated with the cochlea, a cochlear implant with an implanted electrode carrier can electrically stimulate adjacent auditory neural tissue with small currents.

In some patients with some residual hearing in the lower acoustic frequencies, a conventional hearing aid and a cochlear implant can be combined together in a hybrid Electric Acoustic Stimulation (EAS) system. The hearing aid acoustically amplifies lower acoustic frequencies perceived by human ear, while the cochlear implant electrically stimulates the middle and high frequencies. See von Ilberg et al, *Electric-Acoustic Stimulation of the Auditory System*, ORL 61:334-340; Skarzynski et al, *Preservation of Low Frequency Hearing in Partial Deafness Cochlear Implantation (PDCI) Using the Round Window Surgical Approach*, Acta OtoLaryngol 2007; 127:41-48; Gantz & Turner, *Combining Acoustic and Electrical Speech Processing: Iowa/Nucleus Hybrid Implant*, Acta Otolaryngol 2004; 124:344-347; Gstöttner et al., *Hearing Preservation in Cochlear Implantation for Electric Acoustic Stimulation*, Acta Otolaryngol 2004; 124:348-352; all incorporated herein by reference.

FIG. 1 also shows some components of a typical EAS system which includes an external microphone that provides an acoustic signal input to an external signal processor 111 where two different signal processing paths are developed. An upper acoustic frequency range communications signal containing middle and high frequency components is converted into a digital data format, such as a sequence of data frames, for transmission via a transmitter coil 107 over a corresponding implanted receiver coil 106 into the electric implant 108. Besides receiving the processed acoustic information, the electric implant 108 also performs additional signal processing such as error correction, pulse formation, etc., and produces an electric stimulation pattern (based on the extracted acoustic information) that is sent through an electrode lead 109 to an implanted electrode array 110. Typically, this electrode array 110 includes multiple electrode contacts on its outer surface that provide selective electric stimulation of the cochlea 104. The external signal processor 111 also creates a lower acoustic frequency range communications signal to a conventional hearing aid 105 in the ear canal which acoustically stimulates the tympanic membrane 102, and in turn the middle ear 103 and cochlea 104.

Middle ear implants (MEIs) are another alternative hearing prosthesis option for persons with moderate to severe conductive hearing loss who are insufficiently benefited by conventional mechanical hearing aids. Middle ear implants introduce a mechanical stimulation/vibration into the auditory system via a mechanical transducer implanted to an auditory structure in the middle ear, though the exact anatomical location at which this stimulation is delivered varies. For example, due to its small size, the Vibrant Soundbridge (VSB) device with its mechanical stimulator—the Floating Mass Transducer (FMT)—can be coupled to different auditory structures such as the incus, stapes/oval window or the round window. The hearing outcome that is achieved with the VSB strongly depends on the specific auditory coupling geometry. Currently, the hearing improvement with a VSB for frequencies >1 kHz has been shown to be better with coupling to the oval window or round window membranes, whereas lower frequencies are perceived better if the FMT is coupled to the incus.

Figure 3:
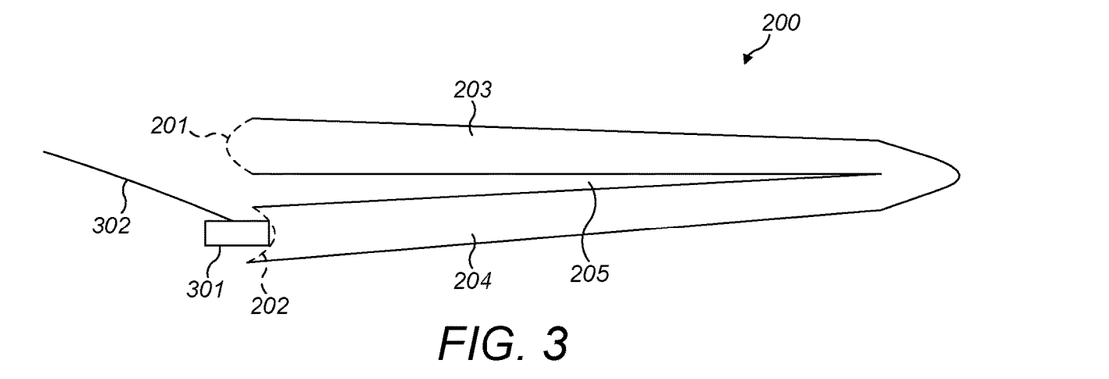
FIG. 3 shows a functional representation of a normal cochlea having a mechanical transducer engaged against the round window membrane.

FIG. 3 shows a simplified example of round window membrane stimulation where a mechanical middle ear stimulator, e.g., a floating mass transducer (FMT) 301 is placed with its flat front side directly in contact with the tissue of the round window membrane 202. Electrical drive signals are delivered from the connecting cable 302 to the FMT 301 which in turns drives the round window membrane 202. Preferably the FMT 301 is placed in the center of the round window membrane 202 where the tissue has its greatest possible elongation. But in existing round window coupling techniques, it is very difficult to determine whether or not the FMT 301 is properly positioned in relation to the round window membrane 202, which is not visually accessible during surgery. For example, the FMT 301 may contact the bone surrounding the round window membrane 202 such that some of the vibrational energy does not enter the cochlea 200. In addition, when the FMT 301 is not orthogonal to the round window membrane 202, that also decreases the amount of vibrational energy entering the cochlea 200. Nonetheless, round window coupling is becoming ever more popular due to good performance with respect to speech recognition, and novel devices are in development for the improvement of this approach (e.g. the Hannover Coupler developed at the Hannover Medical School).

Figure 4A:
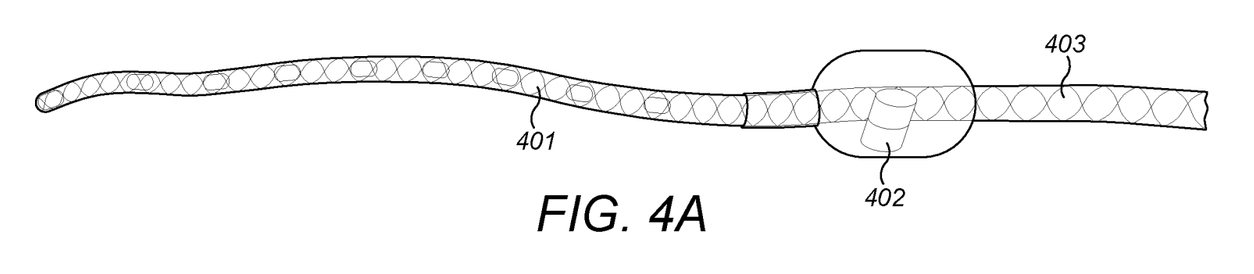
FIGS. 4A-4C show details of prototype CI/FMT stimulation leads.
Figure 4B:
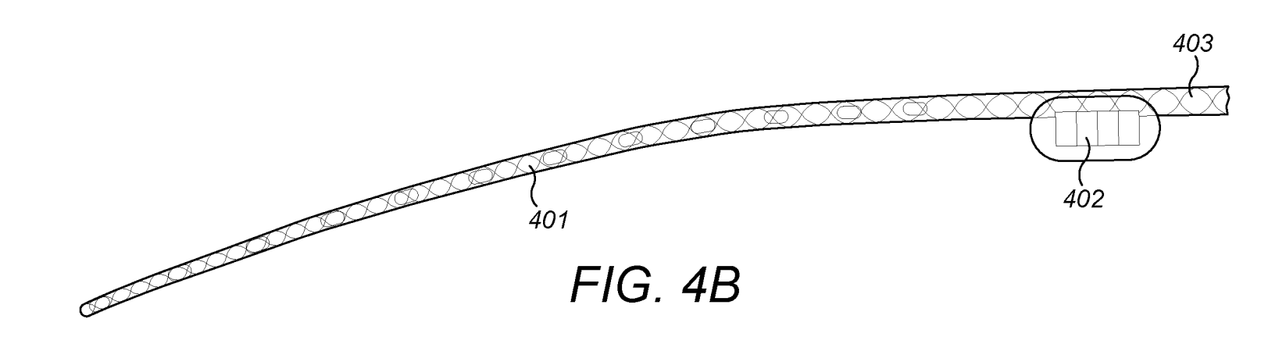
Figure 4C:
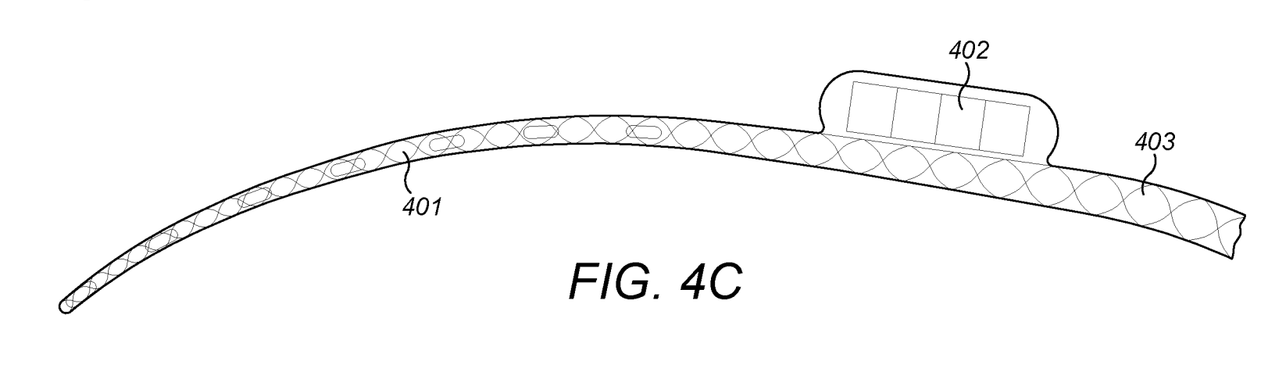

It has also been proposed that an EAS system could use a middle ear FMT for the acoustic mechanical stimulation instead of a conventional hearing aid, forming a CI/FMT system. See, Mueller et al. "Electro-Mechanical Stimulation of the Cochlea by Vibrating Cochlear Implant Electrodes" *Otology & Neurotology* 36.10 (2015): 1753-58; which is incorporated herein by reference in its entirety. For example, as shown in FIGS. 4A-4C, an FMT 402 can be incorporated at the distal end of a cochlear implant electrode lead 403/the base of the electrode array 401 that is inserted into the cochlea via the round window membrane. Experimental results with such a CI/FMT arrangement were lower in amplitude for the FMT stimulation than as with conventional attachment of the FMT to the incus long process, but the loss disadvantage was significantly larger than might have been expected—insufficient vibrational energy is coupled into the cochlea.

SUMMARY

Embodiments of the present invention are directed to a round window coupling device for a hybrid electric-mechanical stimulation hearing implant system. A rigid outer shell has a proximal end, a distal end and an outer surface, and is configured to securely fit into a round window niche in a cochlear outer surface of a recipient patient. An electrode groove is located in the outer surface of the outer shell and is configured to snuggly fit around a portion of a cochlear implant electrode array passing through the round window niche. A coupling filling is enclosed within the outer shell and is configured to couple mechanical vibrations from the proximal end of the outer shell to the distal end of the outer shell with minimal attenuation. A transducer receiver is located at the proximal end of the outer shell and is configured to connect to and receive vibrations from a drive surface of a mechanical transducer (e.g., a floating mass transducer (FMT)). And a drive face is located at the distal end of the outer shell and is configured to interface to perilymph fluid within the cochlea of the recipient patient to deliver vibrations from the coupling filling to the perilymph fluid with minimal attenuation for perception as sound.

In further specific embodiments, the drive face may comprise a drive membrane at the distal end of the outer shell. The coupling filling may comprise a silicone material or a liquid coupling material enclosed within end membranes located at each end of the outer shell. The outer shell may have a cylindrical shape or a frusto-conical shape configured to snuggly fit into the round window niche to securely fix the coupling device and the electrode lead at the round window niche.

Embodiments of the present invention also include a hybrid electric-mechanical stimulation hearing implant system having a round window coupling device according to any of the foregoing.

DETAILED DESCRIPTION

Figure 5A:
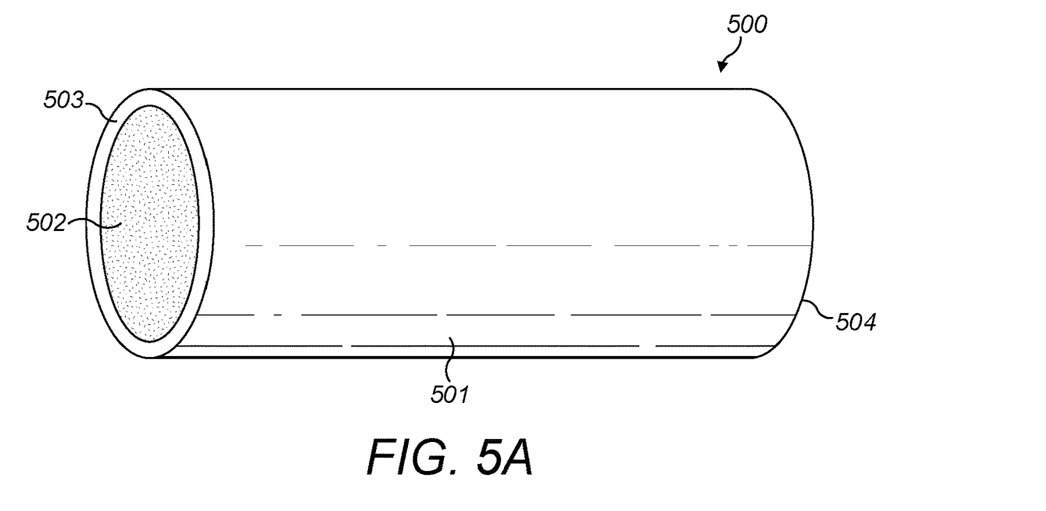
FIGS. 5A-5C show simplified versions of an FMT round window coupling device according to embodiments of the present invention.
Figure 5B:
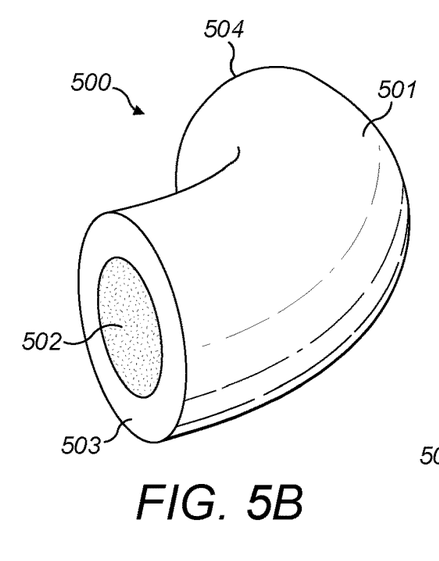
Figure 5C:
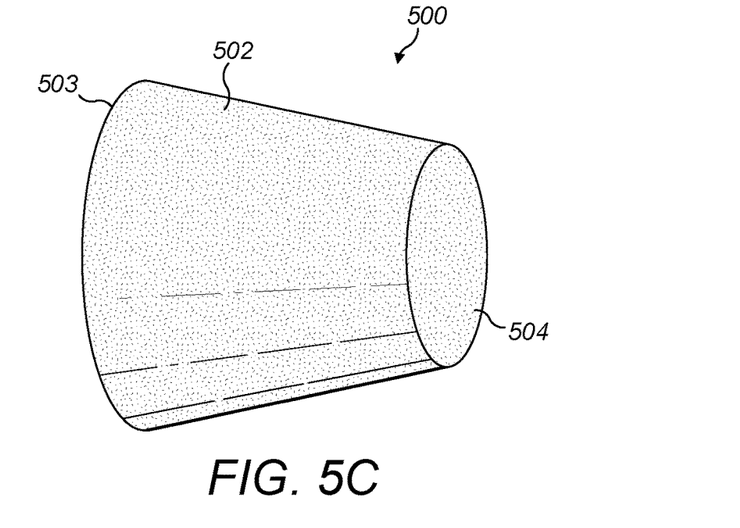

Embodiments of the present invention are directed to a round window coupling device for a hybrid electric-mechanical stimulation hearing implant system that delivers vibrations from a connected middle ear transducer to the perilymph fluid in the cochlea with minimal attenuation. FIGS. 5A-5C show simplified versions of an FMT round window coupling device 500 according to embodiments of the present invention. The coupling device 500 has a rigid outer shell 501 (e.g. a rigid biocompatible polymer material) with a proximal end 503 and a distal end 504 and is configured to securely fit into a round window niche in a cochlear outer surface of a recipient patient.

A transducer receiver (e.g., a recessed receptacle) is located at the proximal 503 end of the outer shell 501 and is configured to connect to and receive vibrations from a drive surface of a mechanical transducer (e.g., a floating mass transducer (FMT)). A coupling filling 502 is enclosed within the outer shell 501 and is configured to couple mechanical vibrations from the proximal end 503 of the outer shell 501 to the distal end 504 of the outer shell 501 with minimal attenuation. For example, the coupling filling 502 may be soft, flexible, but non-compressible silicone material. The elasticity of the coupling filling 502 should be selected so that its natural internal oscillations are maximal within the frequency range of interest—i.e., frequencies at which the patient has reduced sound perception. A drive face is located at the distal end 504 of the outer shell 501 and is configured to interface to perilymph fluid within the cochlea of the recipient patient to deliver vibrations from the coupling filling 502 to the perilymph fluid with minimal attenuation for perception as sound. As shown in FIGS. 5A-5C, the coupling device 500 may have any advantageous specific shape such as generally cylindrical (FIG. 5A) or curved elbow (FIG. 5B). FIG. 5C shows a coupling device 500 having a generally frusto-conical shape that may advantageously configured to snuggly fit into the round window niche to securely fix the coupling device 500 at the round window niche.

Figure 6A:
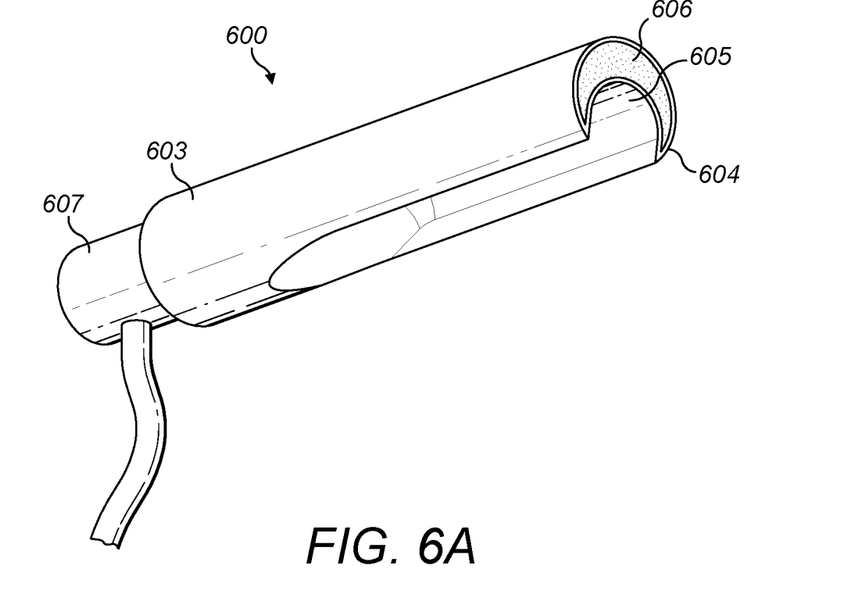
FIGS. 6A-6B show examples of a CI/FMT round window coupling device according to embodiments of the present invention.
Figure 6B:
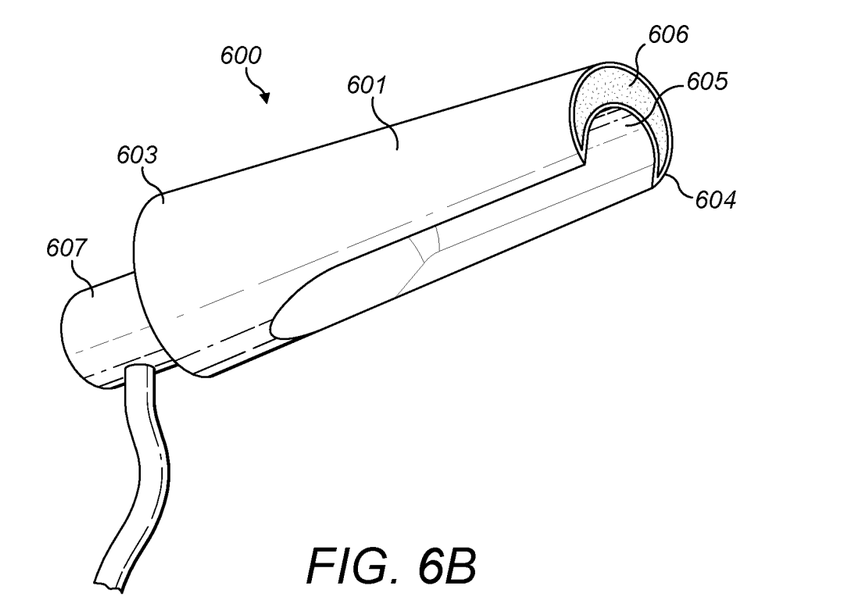

FIGS. 6A-6B show examples of a CI/FMT round window coupling device according to embodiments of the present invention that combine FMT coupling functionality with use of a cochlear implant electrode. In contrast to prior art CI/FMT efforts (e.g., FIGS. 4A-4C), embodiments of the present invention couple all of the mechanical energy of the FMT directly into the perilymph without losses, hence, serving as a decoupler of the FMT's vibrational energy from the electrode array.

The coupling device 600 has a rigid outer shell 601 (e.g. a rigid biocompatible polymer material) with a proximal end 603 and a distal end 604 and is configured to securely fit into a round window niche in a cochlear outer surface of a recipient patient. The coupling device 600 includes an electrode groove 605 that is located in the outer surface of the outer shell 601 and is configured to snuggly fit around a portion of a cochlear implant electrode array passing through the round window niche. In the embodiment shown in FIG. 6A, the coupling device 600 has a generally cylindrical shape, while in the embodiment shown in FIG. 6B, the coupling device 600 has a generally frusto-conical shape configured to snuggly fit into the round window niche to securely fix the coupling device 600 and the connected cochlear implant electrode lead at the round window niche.

A coupling filling is enclosed within the outer shell 601 and couples mechanical vibrations from the proximal end 603 to the distal end 604. Also at the proximal end 603 is an FMT 607 that delivers the mechanical vibrations to the proximal end 603. A drive face 606 is located at the distal end 504 of the outer shell 501 and is configured to interface to perilymph fluid within the cochlea of the recipient patient to deliver vibrations from the coupling filling to the perilymph fluid with minimal attenuation for perception as sound. The coupling filling may be soft, flexible, but non-compressible silicone material as discussed above, or a liquid coupling material enclosed within end membranes located at each end of the outer shell 601, such that the end membrane at the distal end 604 serves as the drive face 606. It will be noted that the coupling device 600, and more specifically the proximal end 603 and/or the FMT 607, can also usefully serve as a handling element to assist the implanting surgeon in controlling the cochlear implant lead during surgery.

Figure 7:
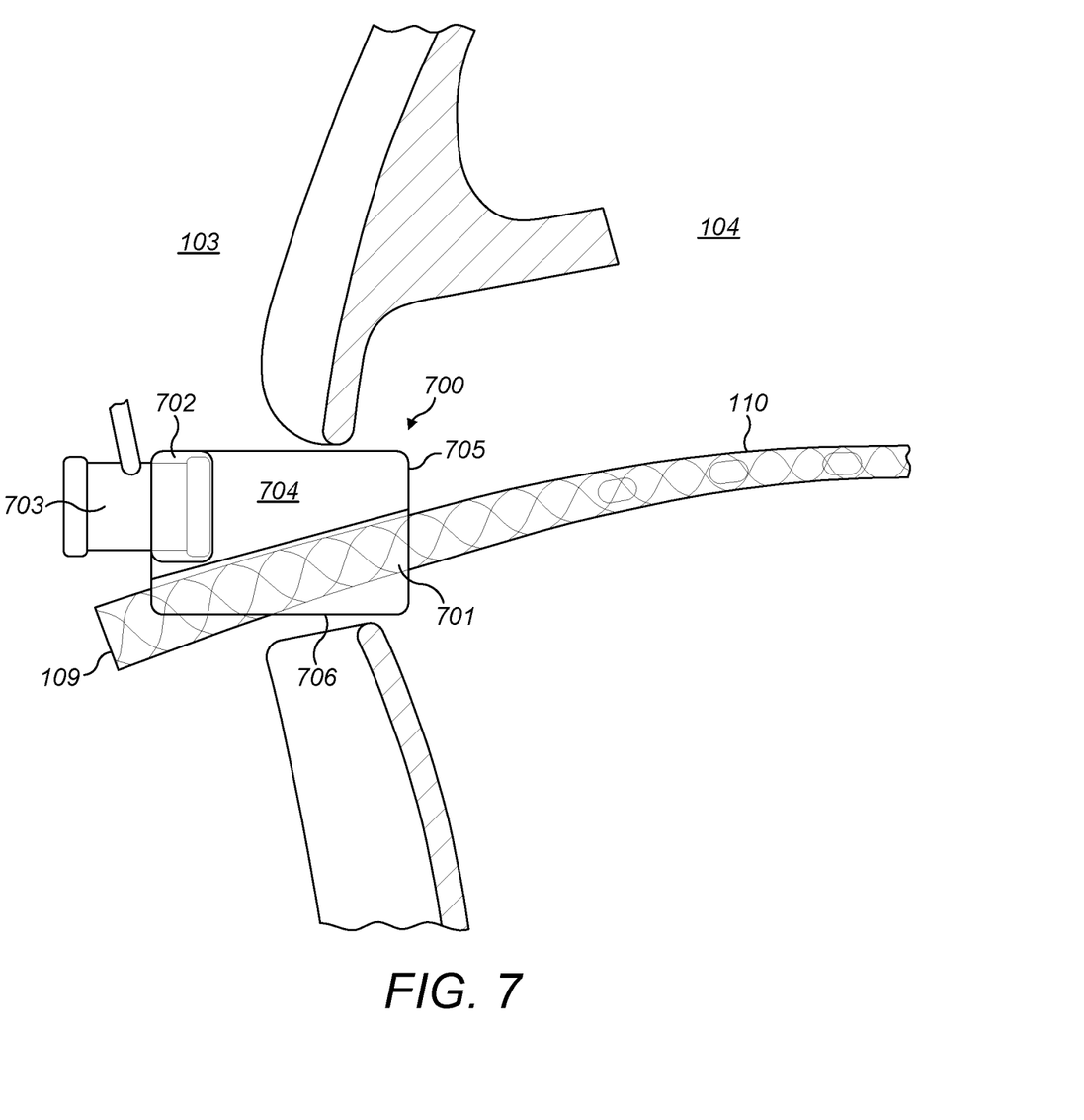
FIG. 7 shows an embodiment of a CI/FMT round window coupling device implanted in a recipient patient according to embodiments of the present invention.

FIG. 7 shows an embodiment of a CI/FMT round window coupling device 700 that is implanted in a recipient patient according to embodiments of the present invention. The coupling device 700 includes a transducer receiver 702 in the specific form of a recessed receptacle located at the proximal end of the coupling device 700 and is configured to connect to and receive vibrations from a drive surface of a mechanical transducer such as a floating mass transducer (FMT) 703 implanted in the middle ear 103. An electrode groove 701 snuggly fits around a distal end portion of a cochlear implant electrode lead 109 for an implanted electrode array 110 that passes through the round window niche into the cochlea 104. A coupling filling 704 is enclosed within the coupling device 700 to couple mechanical vibrations from the connected FMT 703 to the implanted drive surface 705 with minimal attenuation to the perilymph fluid within the cochlea 104.

Although various exemplary embodiments of the invention have been disclosed, it should be apparent to those skilled in the art that various changes and modifications can be made which will achieve some of the advantages of the invention without departing from the true scope of the invention.

What is claimed is:

1. A round window coupling device for a hybrid electric-mechanical stimulation hearing implant system, the device comprising:
    a rigid outer shell having a proximal end, a distal end and an outer surface, and configured to securely fit into a round window niche in a cochlear outer surface of a recipient patient;
    an electrode groove in the outer surface of the outer shell configured to snuggly fit around a portion of a cochlear implant electrode array passing through the round window niche, the cochlear implant electrode array external to the outer shell;
    a coupling filling enclosed within the outer shell and configured to couple mechanical vibrations from the proximal end of the outer shell to the distal end of the outer shell with minimal attenuation;
    a transducer receiver at the proximal end of the outer shell configured to connect to and receive vibrations from a drive surface of a mechanical transducer; and
    a drive face at the distal end of the outer shell configured to interface to perilymph fluid within the cochlea of the recipient patient to deliver vibrations from the coupling filling to the perilymph fluid with minimal attenuation for perception as sound.

2. The coupling device according to claim 1, wherein the drive face comprises a drive membrane at the distal end of the outer shell.

3. The coupling device according to claim 1, wherein the coupling filling comprises non-compressible material.

4. The coupling device according to claim 3, wherein the non-compressible coupling filling comprises a silicone material.

5. The coupling device according to claim 3, wherein the non-compressible coupling filling comprises a liquid coupling material enclosed within end membranes located at each end of the outer shell.

6. The coupling device according to claim 1, wherein the outer shell has a cylindrical shape.

7. The coupling device according to claim 1, wherein the outer shell has a frusto-conical shape configured to snuggly fit into the round window niche to securely fix the coupling device and the electrode lead at the round window niche.

8. The coupling device according to claim 1, wherein the mechanical transducer is a floating mass transducer (FMT).

9. A hybrid electric-mechanical stimulation hearing implant system having a round window coupling device according to any of claims 1-8.

* * * * *